United States Patent
Ryan et al.

(10) Patent No.: US 9,642,664 B2
(45) Date of Patent: May 9, 2017

(54) INSTRUMENT FOR BENDING A BONE FIXATION DEVICE

(71) Applicant: Acumed LLC, Hillsboro, OR (US)

(72) Inventors: Matthew J. Ryan, Beaverton, OR (US); Eric D. Ward, Portland, OR (US); Steven P. Horst, Dayton, OR (US)

(73) Assignee: Acumed LLC, Hillsboro, OR (US)

( * ) Notice: Subject to any disclaimer, the term of this patent is extended or adjusted under 35 U.S.C. 154(b) by 498 days.

(21) Appl. No.: 14/319,908

(22) Filed: Jun. 30, 2014

(65) Prior Publication Data

US 2015/0012003 A1  Jan. 8, 2015

Related U.S. Application Data (60) Provisional application No. 61/842,759, filed on Jul. 3, 2013.

(51) Int. Cl.
  *A61B 17/58* (2006.01)
  *A61B 17/60* (2006.01)
  *A61F 2/00* (2006.01)
  *A61B 17/88* (2006.01)
  *A61B 17/29* (2006.01)

(52) U.S. Cl.
  CPC .. *A61B 17/8863* (2013.01); *A61B 2017/2919* (2013.01)

(58) Field of Classification Search
  None
  See application file for complete search history.

(56) References Cited

U.S. PATENT DOCUMENTS

| | | |
|---|---|---|
| 4,033,388 A | 7/1977 | Ruegger |
| 4,304,117 A | 12/1981 | Rawson |
| 5,373,860 A | 12/1994 | Catone |
| 5,572,899 A | 11/1996 | Balaity et al. |
| 5,651,283 A | 7/1997 | Runciman et al. |
| 6,077,271 A | 6/2000 | Huebner et al. |
| 7,454,939 B2 | 11/2008 | Garner et al. |
| 7,473,257 B2 | 1/2009 | Knöpfle et al. |
| 8,043,298 B2 | 10/2011 | Capanni |
| 2009/0222020 A1 | 9/2009 | Schmuck et al. |
| 2014/0100582 A1* | 4/2014 | Koch ............... A61B 17/8071 606/101 |

OTHER PUBLICATIONS

Depuy Synthes, "Matrix Rib Stable fixation of normal and osteoporotic ribs Surgical Techniques", Jul. 2013, 44 pages.

* cited by examiner

*Primary Examiner* — Sameh Boles
(74) *Attorney, Agent, or Firm* — Kolisch Hartwell, P.C.

(57) ABSTRACT

System, including apparatus and methods, for bending a bone fixation device, such as a bone plate during a surgical procedure. In some embodiments, the system may include an instrument having (a) a clamp with jaws and (b) a graspable handle portion that is manipulable while a bone plate is located between the jaws to bend the bone plate by application of pressure with the jaws at alternating positions along the bone plate. The clamp may allow the bone plate to be reoriented from an orientation for in-plane bending to an orientation for out-of-plane bending, and vice versa, while the bone plate remains between the jaws.

20 Claims, 4 Drawing Sheets

INSTRUMENT FOR BENDING A BONE FIXATION DEVICE

CROSS-REFERENCE TO PRIORITY APPLICATION

This application is based upon and claims the benefit under 35 U.S.C. §119(e) of U.S. Provisional Patent Application Ser. No. 61/842,759, filed Jul. 3, 2013, which is incorporated herein by reference in its entirety for all purposes.

INTRODUCTION

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

To ensure that the skeleton retains its ability to perform its important functions, and to reduce pain and disfigurement, fractured bones should be repaired promptly and properly. Typically, fractured bones are treated using a fixation device that reinforces the bone and keeps bone fragments aligned during healing. Fixation devices may take a variety of forms, including casts for external fixation and bone plates for internal fixation, among others. Bone plates are implantable devices that can be mounted on bone with the plate spanning a fracture. To use a bone plate to repair a fractured bone, a surgeon (1) selects an appropriate plate, (2) reduces (sets) the fracture, and (3) fastens the plate to opposite sides of the fracture using suitable fasteners, such as bone screws, so that pieces of the bone are fixed relative to one another.

The bone plate often is bent intraoperatively by a surgeon to custom-fit the bone plate to the surface contour of a patient's bone. Various surgical instruments have been developed to permit the surgeon to modify the shape of the bone plate for a better match to the bone's surface contour. For example, the surgeon may utilize a pair of separate wrench-like instrument to apply a bending moment to the bone plate. Each instrument may define a slot to receive an edge of the bone plate. In some cases, the bone plate may be held in a vise that replaces one of the instruments.

The surgeon alternatively may prefer a pliers-like instrument to bend the bone plate. The instrument may have a pair of pivotally connected levers each having a handle at one end and a jaw at the other end. A third jaw may be centered about the pivot joint at which the levers are connected. The pliers-like instrument may have the jaws arranged to receive the bone plate for only one type of bending, such as bending out of the plane of the bone plate. Accordingly, the surgeon may need a second bending instrument to introduce lateral, in-plane bends to the same bone plate.

The bending instruments available to a surgeon are inadequate. For example, the instruments can be awkward to use and may not provide sufficient control over the bending process. Accordingly, reshaping a bone plate intraoperatively can be time-consuming and frustrating to the surgeon. A new surgical instrument is needed to bend bone plates.

SUMMARY

The present disclosure provides a system, including apparatus and methods, for bending a bone fixation device, such as a bone plate during a surgical procedure. In some embodiments, the system may include an instrument having (a) a clamp with jaws and (b) a graspable handle portion that is manipulable while a bone plate is located between the jaws to bend the bone plate by application of pressure with the jaws at alternating positions along the bone plate. The clamp may allow the bone plate to be reoriented from an orientation for in-plane bending to an orientation for out-of-plane bending, and vice versa, while the bone plate remains between the jaws.

DETAILED DESCRIPTION

The present disclosure provides a system, including apparatus and methods, for bending a bone fixation device, such as a bone plate during a surgical procedure. In some embodiments, the system may include an instrument having (a) a clamp with jaws and (b) a graspable handle portion that is manipulable while a bone plate is located between the jaws to bend the bone plate by application of pressure with the jaws at alternating positions along the bone plate. The clamp may allow the bone plate to be reoriented from an orientation for in-plane bending to an orientation for out-of-plane bending, and vice versa, while the bone plate remains between the jaws.

In some embodiments, the instrument may include a handle portion that is operatively graspable around a first axis, and an adjustable clamp including a pair of jaws. One of the jaws may be mechanically linked to the handle portion and configured to be driven linearly along a second axis that is transverse to the first axis by manipulation of the handle portion while a bone fixation device is disposed between the jaws, to bend the bone fixation device with the jaws.

The present disclosure also provides a tool (a surgical bending instrument) having a jaw formed by a piston. In some embodiments, the bone fixation device may include a rod that is bent by the instrument. Accordingly, the bone fixation device may be an intramedullary nail, an external fixator rod, a spinal rod, or the like. The bending instrument may have a handle portion (interchangeably termed a handle or handles), such as a pistol grip, that is squeezable to drive the piston against the bone fixation device, for application of a bending moment thereto. The handle may have a spring return that allows the user to quickly and efficiently deform the bone fixation device multiple times by alternately compressing and relaxing the handle.

Alternatively, or in addition, the bending instrument may have a pair of jaws configured to bend a bone plate in each of a pair of orthogonal orientations to introduce in-plane and out-of-plane bends to the bone plate. One of the jaws may function as a guide for longitudinal placement of the bone plate between the jaws by defining at least one opening (such as a pair of openings) to receive the bone plate. Each opening may be shaped to permit the bone plate to be adjusted between orthogonal plate orientations without completely removing the bone plate from the at least one opening and/or from between the jaws. In some cases, one of the jaws may be pivotable about a linear travel axis of the other jaw, to permit adjustment of the orientation of the long axis of the bone fixation device being bent (e.g., from a vertical orientation to a horizontal or other orientation). The bending instrument may offer substantial advantages over bending devices of the prior art, including a more ergonomic design, finer control over the bending process, and/or less manipulation to contour a bone fixation device for a target site on bone.

Further aspects of the present disclosure are described in the following sections: (I) bending instrument with a linear clamp, (II) bending instrument with pivotally connected jaws, and (III) selected embodiments.

I. Bending Instrument with a Linear Clamp

This section describes an exemplary system including (a) a bending instrument having a clamp with jaws that move linearly relative to one another, and (b) an exemplary fixation device in the form of a bone plate; and exemplary configurations of the system; see FIGS. 1-11.

Figure 1:
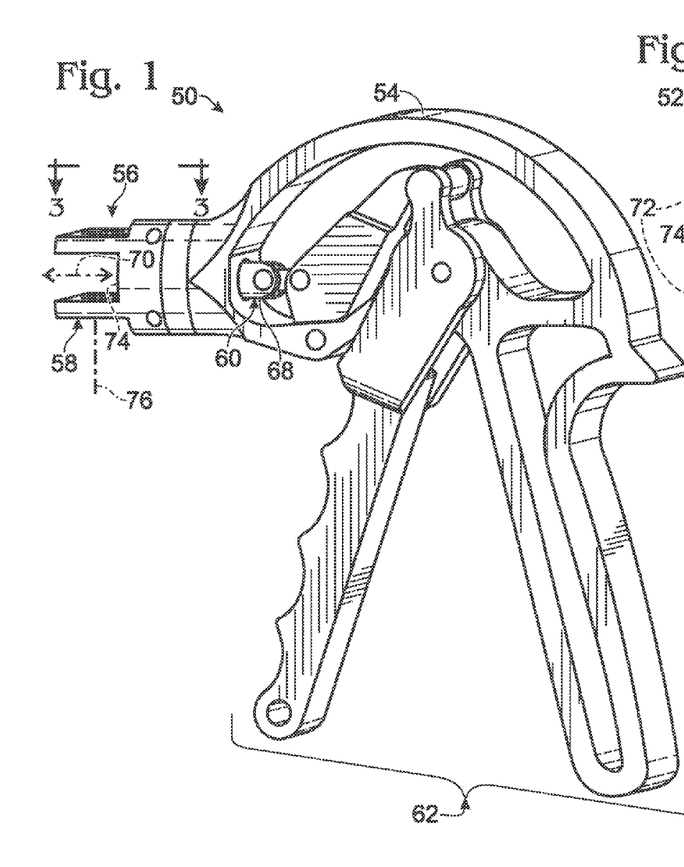
FIG. 1 is a side view of an exemplary instrument for bending a bone fixation device, in accordance with aspects of the present disclosure.
Figure 2:
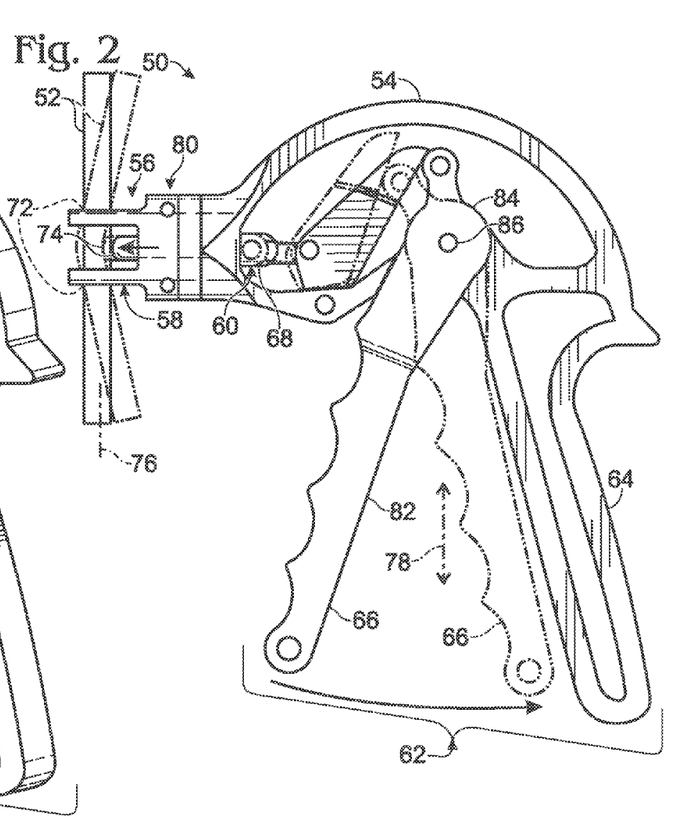
FIG. 2 is an elevational view of the bending instrument of FIG. 1 taken with a bone plate received in a clamp of the instrument, between jaws of the clamp, and illustrating, in phantom outline, exemplary operation of the instrument to bend the bone plate, in accordance with aspects of the present disclosure.

FIGS. 1 and 2 show an exemplary hand-held, manually-powered bending instrument 50 taken in the respective absence and presence of a bone plate 52 and constructed according to aspects of the present disclosure. The bending instrument may have a frame 54 and a clamp 56 supported by the frame. Clamp 56 may be formed by a first clamp member 58 and a second clamp member 60 that are movable relative to one another to cooperatively grip and bend a bone fixation device, such as bone plate 52. A handle portion 62 is connected to frame 54 and may project therefrom. The handle portion is operatively connected to clamp 56, such that clamp 56 can be adjusted (e.g., opened and closed) by manipulation of the handle portion, for example, by compressing a pair of handles 64 and 66 (see FIG. 2). In the depicted embodiment, second clamp member 60 is a piston 68, and squeezing the handles drives linear travel of the piston along a linear travel axis 70 with respect to frame 54 and first clamp member 58.

Clamp 56 has jaws configured to engage bone plate 52 (see FIG. 2). A distal jaw 72, which may be a fixed jaw, is formed by first clamp member 58. A proximal jaw 74, which may be a movable jaw, is formed by second clamp member 60, such as by piston 68. The jaws may face in at least generally opposite directions. For example, in the depicted embodiment, distal jaw 72 faces generally proximally, and proximal jaw 74 faces generally distally. A receiving axis 76 extends through clamp 56 at a position intermediate jaws 72 and 74 and defines a path along which the bone plate may be advanced longitudinally into and/or through clamp 56. The receiving axis may be linear or curved when the clamp is fully opened. The receiving axis is transverse, such as orthogonal, to travel axis 70 (see FIG. 1).

Clamp 56 and handle portion 62 may project in respective transverse directions from frame 54, such as in at least generally orthogonal directions (see FIG. 2). For example, the bending instrument may be operated in the orientation shown, namely, with handle portion 62 projecting downward from frame 54 and operatively graspable with a user's hand around an axis 78, which may be described as a handle axis. The handle axis may be at least generally vertical, such as within about 20 degrees of vertical, and may at least generally bisect the handle portion, as shown in FIG. 2. The bending instrument may form a nose 80 that includes first clamp member 58 and projects distally from the user (and frame 54) and at least generally horizontally from the frame when handle axis 78 is vertical.

Handle portion 62 may be formed by handles 64 and 66 that are respectively fixed and movable with respect to frame 54 (see FIG. 2). Fixed and movable handles 64 and 66 may be arranged proximally and distally, respectively, with respect to a user during operation of bending instrument 50. Movable handle 66 may be operatively connected to piston 68, to provide an actuator 82 that can be manipulated to drive movement of the piston along a travel path (e.g., a linear (proximal-distal) travel axis 70 (see FIG. 1)). For example, movable handle 66 may be provided by a lever 84 that is pivotally connected to frame 54, such as with a pivot pin 86 (see FIG. 2). Accordingly, squeezing handle portion 62 to urge the handles toward each other, generally parallel to travel axis 70, rotates lever 84 to drive proximal jaw 74 of piston 68 distally in nose 80 (and/or first clamp member 58). In other words, compressing (and releasing) the handle portion may cause movable handle 66 and piston 68 to move in at least generally opposite directions relative one another. Travel axis 70 may have a fixed orientation with respect to frame 54 and fixed handle 64. The travel axis may not move with respect to either the frame or the fixed handle as handle portion 62 is manipulated to drive the piston (and proximal jaw 74) along the travel axis.

The handle portion and the piston may be arranged in any suitable relationship. For example, travel axis 70 may be transverse to handle axis 78, such as orthogonal to the handle axis or within about 10, 20, 30, or 45 degrees of orthogonal to the handle axis. The handle portion may be disposed at least predominantly or exclusively on only one side of the travel axis. In other embodiments, travel axis 70 and handle axis 78 may be parallel to one another.

The piston may be any thrustable element, and interchangeably may be called a plunger. The piston may have any suitable cross sectional shape, such as circular, elliptical, polygonal, or the like. The piston may be linear longitudinally or may have longitudinal curvature. The piston may be supported by frame 54 for travel on a linear or curved path with respect to the frame.

A "jaw" is any portion of a clamp configured to engage a bone fixation device while the device is being bent by the clamp. Each jaw may be fixed or movable with respect to a frame of an instrument providing the clamp. The jaw may have any suitable shape, and may be formed by any suitable structure(s), such as one or more plates, rods, blocks or any combination thereof, among others. A pair of jaws may be configured to receive a plate, a rod, a block, and/or the like, to be bent by a clamp of the instrument.

Figure 3:
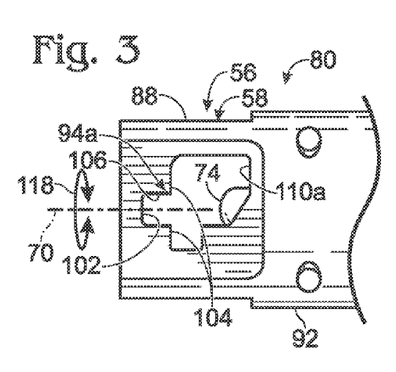
FIG. 3 is a fragmentary plan view of the bending instrument of FIG. 1 taken generally along line 3-3 of FIG. 1 around the clamp.
Figure 4:
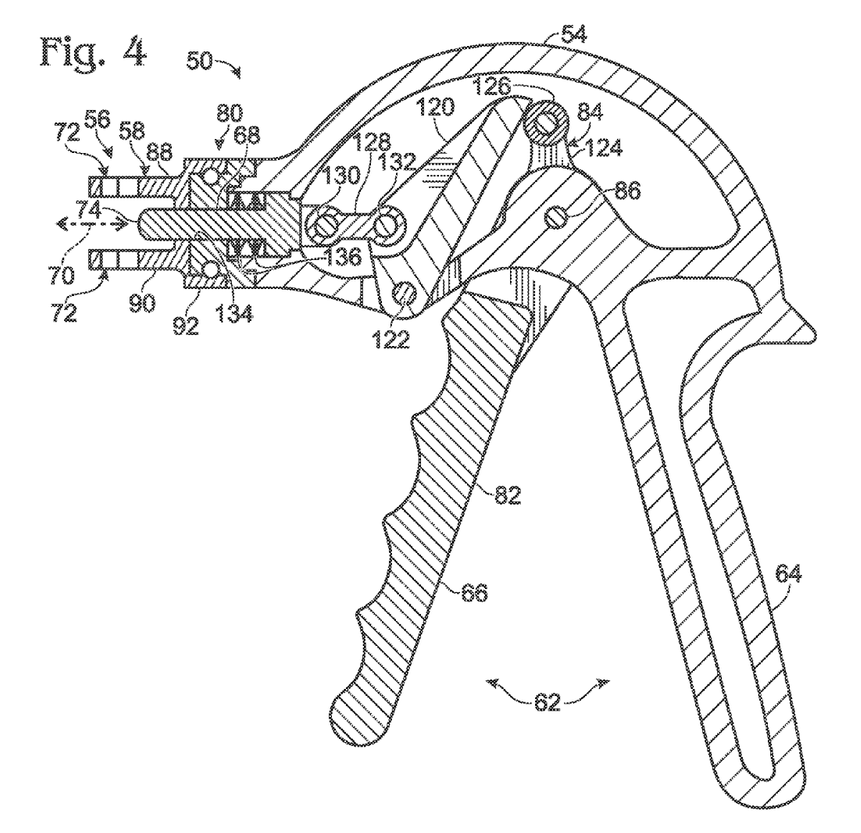
FIG. 4 is vertical sectional view of the bending instrument of FIG. 1 taken through a central plane of the instrument.
Figure 4A:
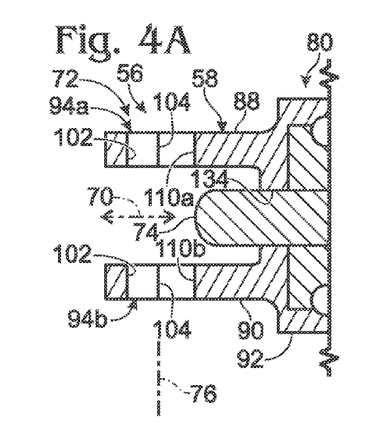
FIG. 4A is a fragmentary sectional view of the bending instrument of FIG. 1 taken as in FIG. 4 around the clamp.

FIGS. 3, 4, and 4A show further aspects of clamp 56. First clamp member 58 may be formed by one or more brackets 88, 90 projecting distally from a base 92. Each bracket 88, 90 may be structured as a cantilever, as shown, or the brackets may be connected to each other distal to base 92. Each bracket may have a plate structure, as shown.

Each bracket 88, 90 may form a respective jaw portion 94a, 94b of distal jaw 72 (see FIGS. 3 and 4A). The jaw portions may be spaced from each other in a direction parallel to receiving axis 76, and each contacts bone plate 52 when the bone plate is being bent. More particularly, jaw portions 94a, 94b and proximal jaw 74 may apply pressure to a bone fixation device, such as a bone plate, at three or more alternating positions along the bone fixation device to apply a bending moment to the bone fixation device.

Figure 5:
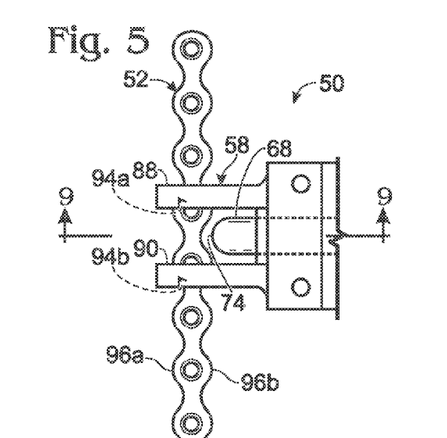
FIG. 5 is a fragmentary elevational view of the bending instrument of FIG. 1 taken around the clamp with a bone plate received between jaws of the clamp in an orientation for bending the bone plate in-plane, and with the bone plate not yet engaged by both jaws of the clamp, in accordance with aspects of the present disclosure.
Figure 6:
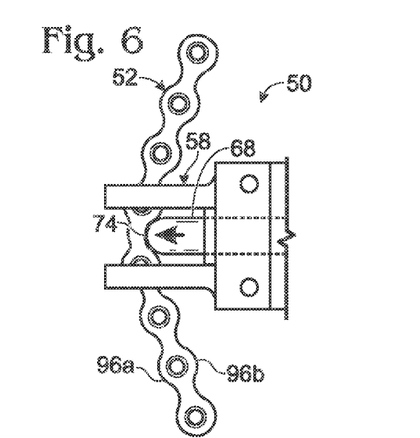
FIG. 6 is another fragmentary elevational view of the bending instrument of FIG. 1, taken as in FIG. 5 with a bone plate, but with each jaw of the clamp pressing against a different longitudinal edge of the bone plate such that the bone plate is being bent in-plane.
Figure 7:
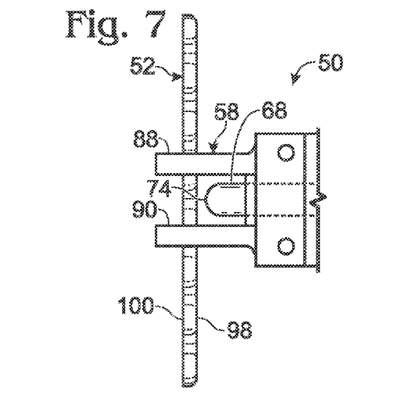
FIG. 7 is yet another fragmentary elevational view of the bending instrument of FIG. 1, taken as in FIG. 5 with a bone plate, but with the bone plate arranged in an orientation for out-of-plane bending by the jaws of the instrument.
Figure 8:
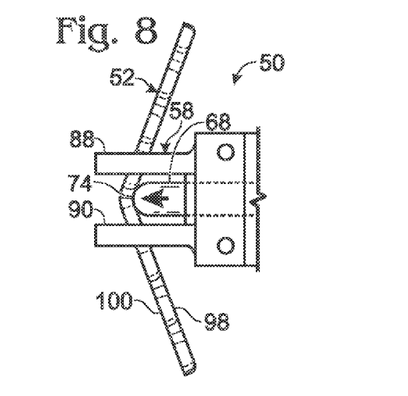
FIG. 8 is still another fragmentary elevational view of the bending instrument of FIG. 1, taken as in FIG. 6 with a bone plate, but with each jaw of the clamp pressing against a top side or a bottom side of the bone plate such that the bone plate is being bent out-of-plane.
Figure 9:
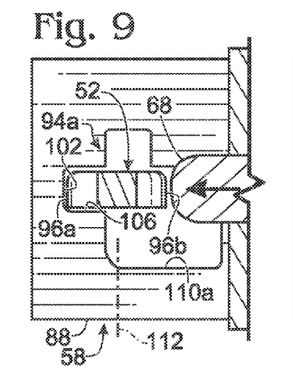
FIG. 9 is a fragmentary sectional view of the bending instrument and bone plate configuration of FIG. 5 taken generally along line 9-9 of FIG. 5.
Figures 10, 11:
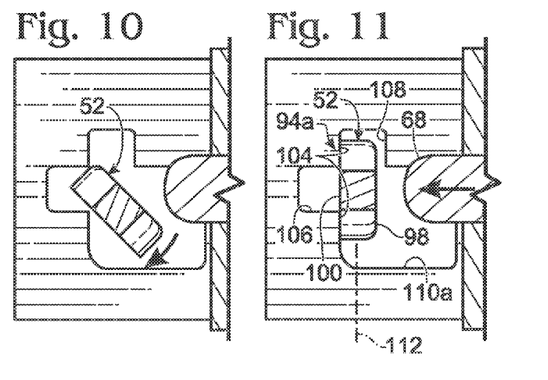
FIG. 10 is another fragmentary sectional view taken generally as in FIG. 9, but as the bone plate is being reoriented about its long axis without removal from the instrument such that the bone plate remains between the jaws.
FIG. 11 is a fragmentary sectional view of the bending instrument and bone plate of FIG. 7 taken generally as in FIG. 9 but after the bone plate has been reoriented for out-of-plane bending while remaining between the jaws of the clamp.

FIGS. 5-9 and 11 illustrate bone plate 52 being bent in-plane (see FIGS. 5, 6, and 9) and out-of-plane (see FIGS. 7, 8, and 11). The orientation of bone plate 52 with respect to the clamp determines how the bone plate is bent.

The bone plate is bent "in-plane" by engaging opposing longitudinal edges 96a, 96b of the bone plate (see FIGS. 5, 6, and 9). Jaw portions 94a, 94b are engaged with one longitudinal edge (96a or 96b). Proximal jaw 74 is engaged with the opposite longitudinal edge at a longitudinal position of the bone plate that is intermediate the longitudinal engagement positions of jaw portions 94a, 94b.

The bone plate is bent "out-of-plane" by engaging opposing top and bottom sides 98, 100 of the bone plate (see FIGS. 7, 8, and 11). Jaw portions 94a, 94b are engaged with one of the sides (bottom side 100 in the depicted configuration). Proximal jaw 74 is engaged with the other side (top side 98 in the depicted configuration) at a longitudinal position of the bone plate that is intermediate the longitudinal engagement positions of jaw portions 94a, 94b. In both the in-plane and out-of-plane orientations, the travel axis of piston 68 (and proximal jaw 74) may be intermediate jaw portions 94a, 94b.

The "top" side of a bone plate faces away from a bone and the "bottom" side of a bone plate faces toward the bone when the bone plate is secured to the bone. The top side may be described as an outer side or outer face. The bottom side may be described as an inner side or inner face. The top and bottom sides can be assigned arbitrarily for a reversible bone plate having no designated outer and inner sides. Longitudinal edges of a bone plate are disposed at least generally at opposite longitudinal perimeter regions of the bone plate, generally between the top and bottom sides of the bone plate, and each may or may not be distinct from and/or smoothly continuous with either or both sides.

Clamp 56 is configured to permit bone plate 52 to be bent in-plane and out-of-plane by adjusting the orientation of the bone plate with respect to the jaws. The orientation of bone plate 52 may be positioned for in-plane bending and out-of-plane bending, in any order, without removal of the bone plate from clamp 56 and/or the bone plate remains between jaws 72, 74 (see FIGS. 9-11). A bone plate is "between the jaws" when at least a portion of the bone plate is located in a space separating the jaws. The plate may remain between the jaws while the bone plate is reoriented for out-of-plane bending after in-plane bending, and vice versa.

Each jaw portion 94a, 94b may form a respective in-plane contact region 102 and a distinct, respective out-of-plane contact region 104 (see FIGS. 3, 4A, 9, and 11). In-plane contact region 102 is configured to engage an edge (96a or 96b) of the bone plate during an in-plane bending procedure (see FIG. 9). The in-plane contact region may be formed at least in part by a recess, such as a notch 106, that receives at least an edge portion of the bone plate (see FIGS. 3 and 9). Out-of-plane contact region 104 is configured to engage top side 98 or bottom side 100 of the bone plate during an out-of-plane bending procedure and may flank notch 106, optionally opposingly (see FIG. 11). In other words, each out-of-plane contact region 104 may include a pair of sub-regions separated by notch 106 (see FIG. 11). Out-of-plane contact region 104 may be formed at least in part by another notch 108 that receives at least an edge portion of the bone plate. In any event, in-plane contact region 102 and out-of-plane contact region 104 may be at least substantially or completely nonoverlapping with one another. Proximal jaw 74 may face in a direction opposite a direction faced by each of contact regions 102 and 104 of each jaw portion 94a, 94b.

First clamp member 58 may define at least one opening to receive a bone fixation device, such as from either end of the bone fixation device. For example, in the depicted embodiment, each bracket 88, 90 defines a respective opening 110*a*, 110*b* to receive bone plate 52 (see FIGS. 3, 4A, 9, and 11). Brackets 88, 90 and/or openings 110*a*, 110*b* of first clamp member 58 may or may not be substantial copies of each other.

Each opening 110*a*, 110*b* may have any suitable structure. Each opening may be closed laterally (i.e., circumferentially bounded), as shown in FIG. 3, such that the bone fixation device only can be placed into the clamp longitudinally (e.g., from either end of the bone plate), or may be open laterally (i.e., not completely bounded circumferentially) to allow the bone fixation device to be placed into the clamp transversely (e.g., from a longitudinal edge of the bone plate). Each opening 110*a*, 110*b* may have a wall defining any combination of in-plane contact region 102, out-of-plane contact region 104, notch 106, and notch 108 for one of jaw portions 94*a*, 94*b*. Alternatively, or in addition, at least one wall region of the opening may function as a stop that limits travel of the bone plate along a transverse axis 112 that is orthogonal to each of axes 70 and 76 (see FIGS. 4A, 9, and 11). For example, opposite side wall regions of notch 106 limit movement of the bone plate parallel to axis 112 in one or both directions parallel to the axis after the bone plate has been received in the notch (see FIG. 9). Opposite wall regions of each opening 110*a*, 110*b* perform a similar function when the bone plate is oriented for out-of-plane bending (see FIG. 11).

First clamp member 58 may be pivotally connected to frame 54 via base 92, which may allow the first clamp member to pivot as a unit about travel axis 70, as indicated at 118 in FIG. 3. Pivotal motion of the first clamp member allows a user to select a suitable or desired direction for receiving axis 76 (and a bone fixation device positioned between jaws 72, 74 of clamp 56). For example, first clamp member 58 is oriented in FIG. 2 with a bone plate extending vertically through instrument 50 and clamp 56, and coplanar with frame 54. First clamp member 58 may, for example, be pivoted such that the bone plate extends horizontally through the clamp (i.e., with the bone plate orthogonal to frame 54), or at any other suitable angle with respect to the frame.

FIG. 4 shows further aspects of a linkage that mechanically links manipulation of handle portion 62 (e.g., via movement of actuator 82) to travel of piston 68 along travel axis 70. The handle portion and the linkage may be described as a mechanical drive assembly for piston 68. Pivotal motion of actuator 82 about pivot pin 86 may cause a corresponding pivotal movement of a link 120 that is pivotally connected to frame 54 by a pivot pin 122. Actuator 82 may be provided by a lever 84 having a short arm 124 opposite the actuator. A roller 126 pivotably mounted on short arm 124 may press against link 120 such that counterclockwise pivotal motion of actuator 82 in FIG. 4 causes a corresponding counterclockwise pivotal motion of link 120 (also see FIG. 2). Piston 68 may be connected to link 120 by a bar 128 and a pair of pivot pins 130, 132 such that pivotal motion of link 120 drives the piston linearly in a piston guide 134 (e.g., a channel). The piston guide may be defined by frame 54, first clamp member 58, or a combination thereof, among others. One advantage of the drive assembly may be that the user has fine control over the position of the piston, for introducing precise changes to the shape of the bone plate. For example, movement of the bottom end of actuator 82 by an actuation distance may produce a travel distance of piston 68 at a ratio (actuation distance:travel distance) of at least about 5:1, 10:1, or 20:1, among others.

The axial position of the piston may be biased proximally, in a direction away from the distal jaw, and toward frame 54 and the user. The position of the piston may be biased by one or more biasing elements 136, such as a plurality of disc springs (Belleville washers), as shown here (see FIG. 4). Accordingly, when pressure on actuator 82 is relaxed, the springs urge the piston proximally (i.e., to the right in FIG. 4). Travel of the piston causes link 120 to pivot and handle portion 62 to return to its relaxed configuration, ready to be compressed again for another cycle of plate bending. In other words, reciprocating travel of the piston and pivotal motion of the actuator may be mechanically linked.

A bone plate may have any suitable structure. The bone plate may be formed as a single piece or may be formed by two or more connected pieces. The bone plate may be linear or nonlinear before being bent, and may be unbranched or branched. The bone plate may define a plurality of holes to receive fasteners, such as bone screws, that secure the bone plate to bone. The bone plate may have a uniform width (or thickness) or may vary in width along the bone plate (and/or may vary in thickness across and/or along the bone plate). The bone plate may be formed of a biocompatible material and may be metal, plastic, or the like.

II. Bending Instrument with Pivotally Connected Jaws

This section describes an exemplary system including (a) a bending instrument 150 having a clamp with pivotally connected jaws and (b) a bone plate 52; and exemplary configurations of the system; see FIGS. 12-16. Instrument 150 may have any suitable combination of features described above for instrument 50 (see FIGS. 1-11).

Figure 12:
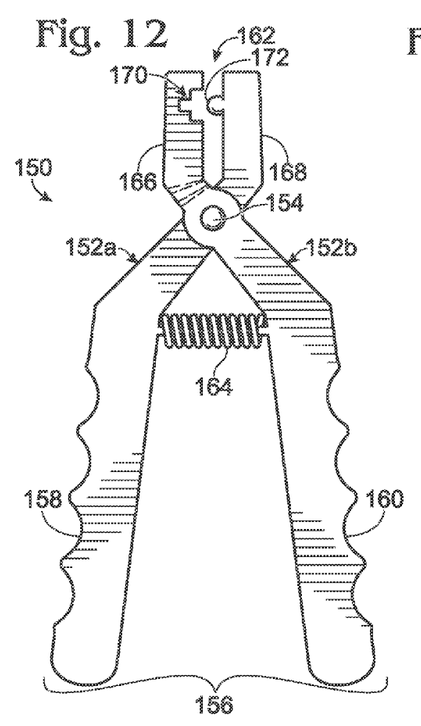
FIG. 12 is an elevational view of another exemplary instrument for bending a bone fixation device, in accordance with aspects of the present disclosure.

FIG. 12 shows instrument 150 in the absence of bone plate 52. The instrument has a pair of levers 152*a*, 152*b* connected by a pivotal connection 154. The levers form a proximal handle portion 156 composed of handles 158, 160. The levers form a clamp 162 distally that is operated by movement of the handles relative to one another. (The clamp is shown in a partially closed configuration.) The clamp may be biased toward an open configuration by a spring 164 connected to the handles.

Clamp 162 includes a first clamp member 166 pivotally connected to a second clamp member 168. First clamp member 166 forms a first jaw 170 that has structural similarity to the distal jaw of instrument 50 (e.g., see FIGS. 3 and 4A). Second clamp member 168 forms a second jaw 172 that has more structural similarity to proximal jaw 74 of instrument 50 (e.g., see FIGS. 3 and 4).

Figure 13:
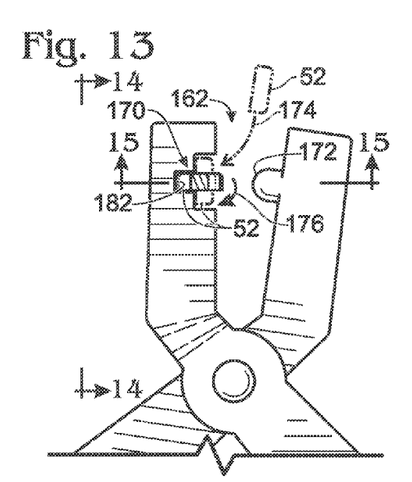
FIG. 13 is a fragmentary view of the instrument of FIG. 12 taken generally as in FIG. 12 around a pair of jaws of the instrument, with the jaws more open than in FIG. 12 and in the presence of a bone plate that is disposed between the jaws and oriented for in-plane bending by the instrument, in accordance with aspects of the present disclosure.

FIG. 13 shows clamp 162 of instrument 150 with the clamp open and bone plate 52 positioned between jaws 170, 172 for in-plane bending (in solid lines) and for out-of-plane bending (in phantom outline). The bone plate may be placed between the jaws, indicated by an arrow at 174, from a longitudinal edge of the bone plate as shown. The bone plate alternatively may be placed between the jaws from an end of the bone plate. In any event, the bone plate may be adjustably oriented, indicated by an arrow at 176, between an orientation for in-plane bending and an orientation for out-of-plane bending, generally by turning the bone plate one-quarter turn. Adjustment of the bone plate between the orientations may be performed without removing the bone plate from the clamp, while the clamp remains in an open configuration.

Figure 14:
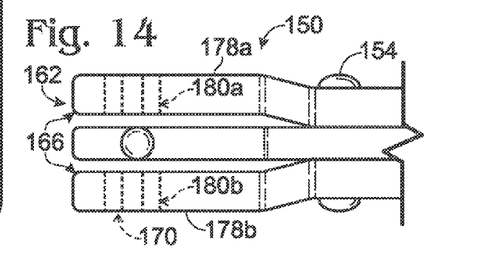
FIG. 14 is another fragmentary view of the instrument of FIG. 12, taken generally along line 14-14 of FIG. 13 toward the jaws in the absence of the bone plate.
Figure 15:
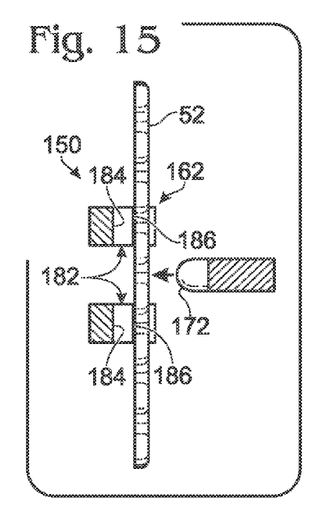
FIG. 15 is still another fragmentary sectional view of the instrument of FIG. 12, taken generally along line 15-15 of FIG. 13 with the bone plate oriented for out-of-plane bending by the instrument.
Figure 16:
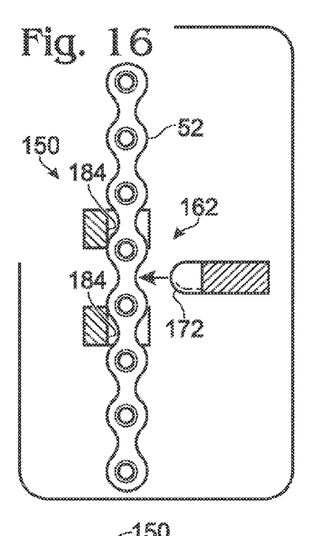
FIG. 16 is yet another fragmentary sectional view of the instrument of FIG. 12, taken as in FIG. 15 except with the bone plate oriented for in-plane bending by the instrument.

FIG. 14 shows another view of clamp 162 taken from a direction orthogonal to that of FIG. 13. First clamp member 166 may include a pair of branches 178a, 178b forming respective jaw portions 180a, 180b of first jaw 170, which are analogous to jaw portions 94a, 94b of instrument 50 (see FIGS. 3 and 4A).

Each branch 178a, 178b may define a respective opening 182 that creates the jaw portion of the branch (see FIGS. 13 and 15) and that is configured to receive a portion of the bone plate. Each opening 182 may be an indentation, as shown, which allows the bone plate to be placed into (and removed from) the indentation by transverse motion of the bone plate. Alternatively, each opening 182 may be a hole that is circumferentially bounded and that necessitates placement of the bone plate into the clamp from an end of the bone plate (e.g., see Section I). In any event, openings 182 may create in-plane contact regions 184 and out-of-plane contact regions 186 as described above for instrument 50 (see FIGS. 13, 15, and 16, and compare with FIGS. 3, 9, and 11).

III. Selected Embodiments

This section describes selected embodiments of the present disclosure, presented as a series of numbered paragraphs.

1. A system for bending a bone fixation device, comprising: an instrument including (i) a clamp having jaws that move linearly relative to one another along a first axis, and (ii) a handle portion operatively graspable around a second axis that is transverse to the first axis, the handle portion including an actuator that is manipulable while a bone fixation device is disposed between the jaws to cause the jaws to apply pressure at alternating positions along the bone fixation device, to bend the bone fixation device.

2. The system of paragraph 1, wherein the instrument includes a frame, and wherein one of the jaws is pivotably connected to the frame for pivotal motion about the first axis.

3. The system of paragraph 1 or paragraph 2, wherein the instrument includes a piston that provides one of the jaws, wherein the handle portion includes a handle and the actuator, and wherein movement of the actuator in a first direction causes the piston to move along the first axis in an at least generally opposite second direction.

4. The system of any of paragraphs 1 to 3, wherein the instrument includes a piston that provides one of the jaws, wherein the handle portion includes a handle and the actuator, and wherein the first axis remains fixed with respect to the handle while the actuator is manipulated to drive the piston along the first axis.

5. The system of any of paragraphs 1 to 4, wherein the first axis is substantially orthogonal to the second axis.

6. A method of fixing bone, the method comprising: deforming a bone fixation device with the instrument of any of paragraphs 1 to 5; and securing the bone fixation device to bone.

7. A system for bending a bone fixation device, comprising: an instrument including (i) a clamp having jaws that move linearly relative to one another along an axis, and (ii) a handle portion including a handle and an actuator that is manipulable while a bone fixation device is disposed between the jaws and while the handle remains fixed with respect to the axis, to cause the jaws to apply pressure at alternating positions along the bone fixation device to bend the bone fixation device.

8. The system of paragraph 7, further comprising the bone fixation device.

9. A method of fixing bone, the method comprising: deforming a bone fixation device with the instrument of paragraph 7 or paragraph 8; and securing the bone fixation device to bone.

10. A system for bending a bone fixation device, comprising: an instrument including (i) a clamp having jaws that move linearly relative to one another along an axis, and (ii) a handle portion compressible while a bone fixation device is disposed between the jaws to cause the jaws to apply pressure at alternating positions along the bone fixation device, to bend the bone fixation device, wherein the instrument is orientable such that the axis is horizontal and the handle portion is operatively graspable below the axis.

11. The system of paragraph 10, further comprising the bone fixation device.

12. A method of fixing bone, the method comprising: deforming a bone fixation device with the instrument of paragraph 10 or paragraph 11; and securing the bone fixation device to bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for bending a bone plate, comprising:
a bone plate; and
an instrument including (a) a clamp having jaws and (b) a graspable handle portion that is manipulable while the bone plate is between the jaws to bend the bone plate by application of pressure with the jaws at alternating positions along the bone plate;
wherein the clamp allows the bone plate to be reoriented from an orientation for in-plane bending to an orientation for out-of-plane bending while the bone plate remains between the jaws,
wherein the jaws include a first jaw and a second jaw, and wherein the first jaw is configured such that each region of the first jaw that applies pressure to the bone plate when the bone plate is bent in-plane is out of contact with the bone plate when the bone plate is bent out-of-plane.

2. The system of claim 1, wherein the clamp allows the bone plate to stay generally parallel to a transverse axis of the instrument when the bone plate is reoriented from the orientation for in-plane bending to the orientation for out-of-plane bending.

3. The system of claim 1, wherein one of the jaws is formed at least in part by an opening including a notch, wherein a portion of the bone plate is received in the opening when the bone plate is in the orientation for in-plane bending and when the bone plate is in the orientation for out-of-plane bending, and wherein the bone plate extends substantially into the notch when the bone plate is in the orientation for in-plane bending but not when the bone plate is in the orientation for out-of-plane bending.

4. The system of claim 1, wherein the bone plate has opposing ends and opposing longitudinal edges that extend to each opposing end, and wherein the clamp is configured to receive the bone plate from either opposing end of the bone plate but not from either opposing longitudinal edge.

5. The system of claim 1, wherein the second jaw is configured such that a same region of the second jaw contacts the bone plate when the bone plate is bent in-plane and out-of-plane.

6. The system of claim 1, wherein manipulation of the handle portion causes linear motion of the jaws relative to one another.

7. The system of claim 1, wherein manipulation of the handle portion causes pivotal motion of the jaws relative to one another.

8. The system of claim 1, wherein compression of the handle portion causes the jaws to move relative to one another.

9. A method of bending a bone plate in the system of claim 1, the method comprising:
  placing the bone plate of claim 1 between the jaws of the instrument of claim 1, with the bone plate oriented for bending the bone plate in a first direction;
  bending the bone plate in the first direction by application of pressure with the jaws at alternating positions along the bone plate;
  reorienting the bone plate for bending the bone plate in a second direction that is orthogonal to the first direction, while the bone plate remains between the jaws; and
  bending the bone in the second direction by application of pressure with the jaws at alternating positions along the bone plate.

10. The method of claim 9, wherein pressure is applied by the jaws at three or more alternating positions on opposing longitudinal edges of the bone plate to bend the bone plate in-plane, and wherein pressure is applied at three or more alternating positions on top and bottom sides of the bone plate to bend the bone plate out-of-plane.

11. The method of claim 9, wherein the step of reorienting includes a step of turning the bone plate one-quarter turn, generally about a long axis of the bone plate.

12. The method of claim 9, wherein each of the steps of bending includes a step of driving linear movement of the jaws relative to one another.

13. The method of claim 9, wherein one of the jaws is formed at least in part by an opening including a notch, wherein a portion of the bone plate is received in the opening when the bone plate is bent in-plane and when the bone plate is bent out-of-plane, and wherein the bone plate extends substantially into the notch when the bone plate is bent in-plane but not when the bone plate is bent out-of-plane.

14. A system for bending a bone fixation device, comprising:
  an instrument including
    a clamp having jaws that move linearly relative to one another along a first axis, and
    a handle portion operatively graspable around a second axis that is transverse to the first axis, the handle portion including an actuator that is manipulable while a bone fixation device is disposed between the jaws to cause the jaws to apply pressure at alternating positions along the bone fixation device, to bend the bone fixation device;
  wherein one of the jaws is formed at least in part by an opening including a notch, wherein a portion of the bone fixation device is received in the opening when the bone fixation device is in the orientation for in-plane bending and when the bone fixation device is in the orientation for out-of-plane bending, and wherein the bone fixation device extends substantially into the notch when the bone fixation device is in the orientation for in-plane bending but not when the bone fixation device is in the orientation for out-of-plane bending.

15. The system of claim 14, further comprising the bone fixation device.

16. The system of claim 14, wherein the handle portion is disposed at least predominantly on only one side of the first axis.

17. The system of claim 14, wherein the instrument is orientable such that the first axis is horizontal and the handle portion is graspable around an at least generally vertical axis.

18. The system of claim 14, wherein the instrument is orientable such that the first axis is horizontal and the handle portion is operatively graspable below the first axis.

19. A method of fixing bone, the method comprising:
  deforming a bone fixation device using the system of claim 14; and
  securing the bone fixation device to bone.

20. A system for bending a bone plate, comprising:
  a bone plate; and
  an instrument including (a) a clamp having jaws and (b) a graspable handle portion that is manipulable while the bone plate is between the jaws to bend the bone plate by application of pressure with the jaws at alternating positions along the bone plate;
  wherein the clamp allows the bone plate to be reoriented from an orientation for in-plane bending to an orientation for out-of-plane bending while the bone plate remains between the jaws,
  wherein one of the jaws is formed at least in part by an opening including a notch, wherein a portion of the bone plate is received in the opening when the bone plate is in the orientation for in-plane bending and when the bone plate is in the orientation for out-of-plane bending, and wherein the bone plate extends substantially into the notch when the bone plate is in the orientation for in-plane bending but not when the bone plate is in the orientation for out-of-plane bending.

* * * * *